US010445869B2

(12) United States Patent
Ioachim (10) Patent No.: US 10,445,869 B2
(45) Date of Patent: Oct. 15, 2019

(54) ONLINE INSPECTION FOR COMPOSITE STRUCTURES

(71) Applicant: BOMBARDIER INC., Dorval (CA)

(72) Inventor: Octavian Ioachim, Pointe-Claire (CA)

(73) Assignee: BOMBARDIER INC., Dorval (CA)

( * ) Notice: Subject to any disclaimer, the term of this patent is extended or adjusted under 35 U.S.C. 154(b) by 8 days.

(21) Appl. No.: 15/532,799

(22) PCT Filed: Nov. 30, 2015

(86) PCT No.: PCT/IB2015/059223
§ 371 (c)(1),
(2) Date: Jun. 2, 2017

(87) PCT Pub. No.: WO2016/088024
PCT Pub. Date: Jun. 9, 2016

(65) Prior Publication Data
US 2017/0365049 A1    Dec. 21, 2017

Related U.S. Application Data

(60) Provisional application No. 62/086,970, filed on Dec. 3, 2014.

(51) Int. Cl.
*G06T 7/00* (2017.01)
*B29C 70/38* (2006.01)
(Continued)

(52) U.S. Cl.
CPC ............ *G06T 7/0004* (2013.01); *B28B 1/523* (2013.01); *B28B 17/0072* (2013.01);
(Continued)

(58) Field of Classification Search
CPC ... G06T 7/0004; B28B 1/523; B28B 17/0072; B29C 70/384; B29C 70/388; B29C 70/54; G01N 21/8806; H04N 5/2256
See application file for complete search history.

(56) References Cited

U.S. PATENT DOCUMENTS 5,562,788 A    10/1996  Kitson et al.
6,075,883 A *  6/2000   Stern .................. G01N 21/8806
                                               382/144

(Continued)

FOREIGN PATENT DOCUMENTS

EP    1391721    2/2004
EP    1503206    2/2005
(Continued)

OTHER PUBLICATIONS

International Search Report and Written Opinion issued in PCT Application No. PCT/IB2015/059223.
(Continued)

*Primary Examiner* — John R Schnurr
(74) *Attorney, Agent, or Firm* — Norton Rose Fulbright Canada LLP (57) ABSTRACT

There is described an online inspection method and system having an illumination system that provides bright-field and dark-field illumination concurrently or sequentially, at varying intensities, in order to acquire images that may be read by an image processing device. The image processing device may obtain measurements of features in the images and evaluate acceptability of the features.

20 Claims, 7 Drawing Sheets

(51) Int. Cl.
    *G01N 21/88*     (2006.01)
    *B28B 1/52*     (2006.01)
    *B28B 17/00*     (2006.01)
    *B29C 70/54*     (2006.01)
    *H04N 5/225*     (2006.01)
    *G01N 21/84*     (2006.01)
    *B29K 105/06*     (2006.01)

(52) U.S. Cl.
    CPC .......... *B29C 70/384* (2013.01); *B29C 70/388* (2013.01); *B29C 70/54* (2013.01); *G01N 21/8806* (2013.01); *H04N 5/2256* (2013.01); *B29K 2105/06* (2013.01); *G01N 2021/8472* (2013.01); *G01N 2021/8825* (2013.01); *G06T 2207/30164* (2013.01)

(56) References Cited

U.S. PATENT DOCUMENTS

| | | |
|---|---|---|
| 6,290,382 B1 | 9/2001 | Bourn et al. |
| 6,741,335 B2 | 5/2004 | Kinrot et al. |
| 6,960,769 B2 | 11/2005 | Burk et al. |
| 7,659,973 B2 | 2/2010 | Furman et al. |
| 7,889,907 B2 | 2/2011 | Engelbart et al. |
| 8,377,239 B2 | 2/2013 | Engelbart et al. |
| 8,426,223 B2 | 4/2013 | Voges et al. |
| 8,759,116 B2 | 6/2014 | Schultz et al. |
| 9,299,118 B1* | 3/2016 | McGraw ................ G01B 11/02 |
| 2005/0025350 A1* | 2/2005 | Engelbart .............. B29C 70/54 382/141 |
| 2005/0094021 A1* | 5/2005 | Gorlik ................ H04N 5/23212 348/345 |
| 2005/0022575 A1 | 10/2005 | Engelbart et al. |
| 2005/0225753 A1* | 10/2005 | Engelbart ............. B29C 70/384 356/237.1 |
| 2006/0152712 A1* | 7/2006 | Engelbart .......... G01N 21/8806 356/237.1 |
| 2011/0017381 A1 | 1/2011 | Oldani |
| 2013/0077159 A1* | 3/2013 | Tani ...................... G02B 21/125 359/387 |
| 2013/0169789 A1* | 7/2013 | Lee ........................ G01N 21/95 348/87 |
| 2014/0098560 A1* | 4/2014 | Brukilacchio ........ A61B 1/0653 362/555 |
| 2014/0210946 A1 | 7/2014 | Hsiao |

FOREIGN PATENT DOCUMENTS

| | | |
|---|---|---|
| JP | H11108637 | 4/1999 |
| KR | 20140031372 | 3/2014 |

OTHER PUBLICATIONS

Christina Krombholz et al., "Improving the production quality of the advances automated fiber placement process by means of online path correction" 28th International congress of the aeronautical sciences, 2012, pp. 1-10.

Office Action dated Aug. 29, 2018 in connection with corresponding Chinese patent application No. 201580065638.6.

* cited by examiner

ONLINE INSPECTION FOR COMPOSITE STRUCTURES

CROSS-REFERENCE TO RELATED APPLICATIONS

This application claims priority under 35 U.S.C. 119(e) of U.S. Provisional Patent Application No. 62/086,970, filed on Dec. 3, 2014 and entitled "Online Inspection for Composite Structures", the contents of which are hereby incorporated by reference.

TECHNICAL FIELD

The present invention relates to the field of machine vision inspection and more particularly, to an online inspection/measurement system that is able to obtain measurements of features of a surface of a composite component in order to evaluate the acceptability of the features.

BACKGROUND OF THE ART

Composite structures (or components) are generally made from two or more constituent materials with significantly different physical or chemical properties. When combined, they produce a structure with characteristics different from the individual materials, with the aim of using the benefit of both.

When manufacturing composite structures using a manufacturing process such as Automated Fiber Placement (AFP) or Automated Tape Layering (ATL), inspecting the dimensional requirements of the manufactured structures is an important part of the manufacturing process. At least part of the inspection process is done on freshly laid fiber. It is very difficult to obtain high quality images from such surfaces due to the different directional reflectivity of the fibers. In addition, the features to be inspected are black details on black background, thus producing poor contrast.

For these reasons, known methods for performing dimensional inspection involve gathering data via manual inspection using a hand-held laser tracker, and having an operator compare the measured data with theoretical data from a Computer-Aided Design (CAD) file. In the case of a composite structure having many plies, manual inspection of the fibers of each ply of the structure is extremely time consuming. Another shortcoming of manual inspection is that it is dependent on the hand and eye skills of the operator, which makes it harder to validate the inspection at a later time.

There is therefore a need to improve the inspection phase of the manufacturing process for certain structures.

SUMMARY

There is described an online inspection method and system having an illumination system that provides bright-field and dark-field illumination concurrently or sequentially, at varying intensities, in order to acquire images that may be read by an image processing device. The image processing device may obtain measurements of features in the images and evaluate acceptability of the features.

In accordance with a first broad aspect, there is provided a system for online inspection of a composite structure manufactured by an automated tool. The system comprises an image acquisition device in proximity to a head of the tool above a surface of the composite structure and defining a field of view on the surface of the composite structure, the image acquisition device and the surface of the composite structure defining a bright-field illumination zone and a dark-field illumination zone; and an illumination system positioned above the surface of the composite structure. The illumination system comprises a top illumination light source inside the bright-field illumination zone, for projecting light at a first intensity onto the surface of the composite structure within the field of view that is reflected by the surface towards the image acquisition device; and a side illumination light source inside the dark-field illumination zone, for projecting light at a second intensity different from the first intensity onto the surface of the composite structure within the field of view that is reflected by the surface away from the image acquisition device.

In some embodiments, the system further comprises an optical adapter positioned between the image acquisition device and the surface of the composite structure for spacing the image acquisition device from the surface and/or directing a vision axis of the image acquisition device substantially perpendicularly to the surface. In some embodiments, an enclosure houses the optical adapter and the illumination system and is coupled to the image acquisition device.

In some embodiments, the image acquisition device comprises a lens having a long focal length F and a corresponding viewing distance D. In some embodiments, the long focal length F is at least five times longer than a diagonal of one of a film plane and a digital sensor of the image acquisition device. In some embodiments, the viewing distance D is at least twenty times longer than the diagonal of one of the film plane and the digital sensor of the image acquisition device.

In some embodiments, at least one of the top illumination light source and the side illumination light source comprises an array of Light Emitting Diodes (LEDs). In some embodiments, the array of LEDs is at least one of curved and composed of LEDs of varying intensities. In some embodiments, the LEDS comprise flash LEDs. In some embodiments, at least one of the top illumination light source and the side illumination light source comprises a backlighting plate.

In some embodiments, at least one of the top illumination light source and the side illumination light source projects colored light onto the surface. In some embodiments, the colored light is one of red-orange and blue.

In some embodiments, the image acquisition device comprises a shutter time synchronized with a response time of the illumination system.

In accordance with another broad aspect, there is provided a method for online inspection of a composite structure manufactured by an automated tool. The method comprises illuminating a surface of the composite structure by projecting light at a first intensity onto the surface of the composite structure from a top illumination light source and projecting light at a second intensity different from the first intensity onto the surface of the composite structure from a side illumination light source. The method also comprises acquiring an image of the illuminated surface of the composite structure using an image acquisition device in proximity to a head of the automated tool, the image acquisition device and the surface of the composite structure defining a bright-field illumination zone comprising the top illumination light source and a dark-field illumination zone comprising the side illumination light source.

In some embodiments, the method further comprises directing a vision axis of the image acquisition device substantially perpendicularly to the surface with an optical adapter. The optical adapter may also be used to space the image acquisition device from the surface. In some embodiments, the optical adapter and the illumination system are comprised in an enclosure coupled to the image acquisition device.

In some embodiments, acquiring an image comprises acquiring the image with a long focal length F and a corresponding viewing distance D. In some embodiments, the long focal length F is at least five times longer than a diagonal of one of a film plane and a digital sensor of the image acquisition device. In some embodiments, the viewing distance D is at least twenty times longer than the diagonal of one of the film plane and the digital sensor of the image acquisition device.

In some embodiments, at least one of the top illumination light source and the side illumination light source comprises an array of Light Emitting Diodes (LEDs). In some embodiments, the array of LEDs is at least one of curved and composed of LEDs of varying intensities. In some embodiments, the LEDS comprise flash LEDs. In some embodiments, at least one of the top illumination light source and the side illumination light source comprises a backlighting plate.

In some embodiments, illuminating the surface of the composite component comprises projecting colored light onto the surface. In some embodiments, the colored light is one of red-orange and blue.

In some embodiments, acquiring at least one image comprises acquiring a sequence of multiple images, each one with a different and customized illumination strategy applied in accordance with a specific local morphology of the surface of the composite structure.

In some embodiments, illuminating the surface of the composite structure comprises projecting light at the first intensity and projecting light at the second intensity in a sequential manner.

In this specification, a lens said to have a "long focal length" is intended to mean that it magnifies the image of the subject, such as a telephoto lens or a super telephoto lens. As the focal length of the lens increases, the depth of field gets shallower (for a same viewing distance) and the angle of view is narrower. As such, the term long focal length refers to the relationship between the absolute focal length of the lens and the diagonal of the film image. In some embodiments, the long focal length is provided from about 70 mm to about 300 mm. In some embodiments, the long focal length is provided from about 135 mm to about 300 mm. In some embodiments, the long focal length comprises a focal length greater than or equal to about 70 mm. In some embodiments, the long focal length is at least five times longer than the diagonal of a sensor provided in the image acquisition device. In some embodiments, a viewing distance for a long focal length is at least twenty times longer than the diagonal of the sensor provided in the image acquisition device.

BRIEF DESCRIPTION OF THE DRAWINGS

Further features and advantages of the present invention will become apparent from the following detailed description, taken in combination with the appended drawings, in which.

It will be noted that throughout the appended drawings; like features are identified by like reference numerals.

DETAILED DESCRIPTION

A method and system for online inspection of a composite structure manufactured by an automated tool will be described. For illustrative purposes, the tool described is an Automated Fiber Placement (AFP) machine but other automated manufacturing tools, such as Automated Tape Layering (ATL) machines, may be used. In order to manufacture a composite structure using AFP, fiber strips (tows) are laid along a mold in multiple layers in order to create a composite structure having the shape of the mold. The fiber strips are placed along the mold in accordance with fiber laying trajectories that are input into the AFP machine to create a given structure in accordance with a set of design parameters. Some of the features that may be inspected include, but are not limited to, fiber gaps, fiber overlap, angle deviations, debris, and tow positions.

The composite structure may comprise various materials, such as but not limited to cements, concrete, reinforced plastics, metal composites and ceramic composites. For example, the composite structure may be composed of composite fiber-reinforced plastics. The composite structure may be used for various applications, including but not limited to buildings, bridges, space crafts, aircrafts, watercrafts, land vehicles including railway vehicles, and structures such as wind turbine blades, swimming pool panels, bathtubs, storage tanks, and counter tops.

Figure 1:
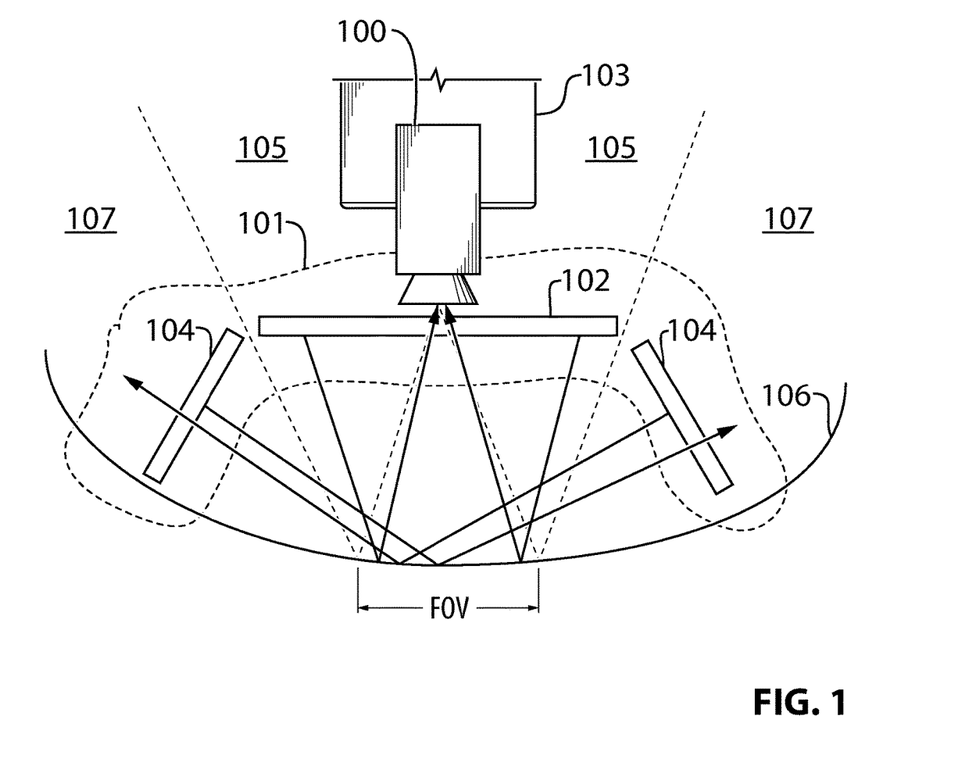
FIG. 1 is a schematic diagram of an exemplary system for online inspection of a composite structure manufactured by an automated tool.

The system for online inspection of a composite structure manufactured by an automated tool generally comprises an image acquisition device 100 and an illumination system 101, as illustrated in FIG. 1. The image acquisition device 100 may be any instrument that records images that can be stored directly, transmitted to another location, or both. For example, the image acquisition device 100 may be a video camera, a still camera, a digital camera, an image sensor, a CCD sensor, a CMOS sensor, and an active pixel sensor, among other possibilities.

Images are processed by an image processor (not shown) to perform inspection in real time or substantially real time, i.e. as each layer is being laid upon the mold to form the composite structure. The image acquisition device 100 is mounted to a head of the automated tool 103 and defines a field of view (FOV) on a surface of the composite structure 106. Also defined by the image acquisition device 100 and the surface of the composite structure 106 are a bright-field illumination zone 105 and a dark-field illumination zone 107. The bright-field illumination zone 105 is the area above the composite structure surface 106 where light emitted from a light source and projected within the FOV will be reflected into the image acquisition device 100. The dark-field illumination zone 107 is the area above the composite structure surface 106 where light emitted from a light source and projected within the FOV will be reflected away from the image acquisition device 100. One or more top illumination light sources 102 is provided inside the bright-field illumination zone 105. One or more side illumination light source 104 is provided inside the dark-field illumination zone 107. In some embodiments, four side illumination lights sources 104 are provided, namely a front side source, a back side source, a left side source, and a right side source.

The illumination system 101 is thus a combination of dark-field light and bright-field light and is provided in order to reveal sufficient details available on the surface 106 of the composite structure to ensure that an image captured by the image acquisition device 100 may contain enough information to be successfully processed by an image processor. The side illumination light source 104 is provided at a first intensity and is used to create high contrast images from shadows, i.e. highlight the surface details. However, too much shadow prevents accurate measurement from the image processor. While a human operator may be able to distinguish more easily the defects in a high contrast image, excess shadow may be problematic for an image processor. The top illumination light source 102 is thus provided at a second intensity different from the first intensity to fill the edges of the shadows created by the side illumination light source 104 so that these edges are not mistaken by the image processor as real features.

Figure 2A:
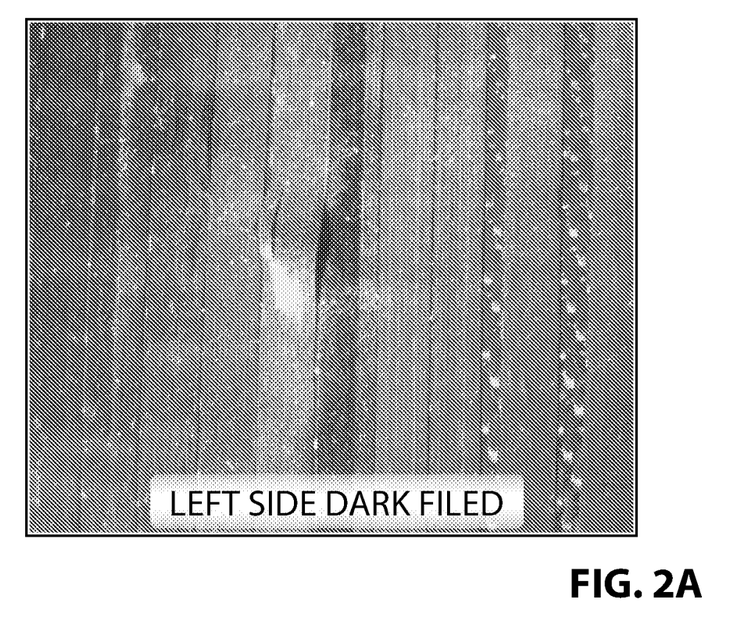
FIG. 2a is an exemplary image of the surface of a composite component captured while the surface is illuminated with only left side dark-field illumination.
Figure 2B:
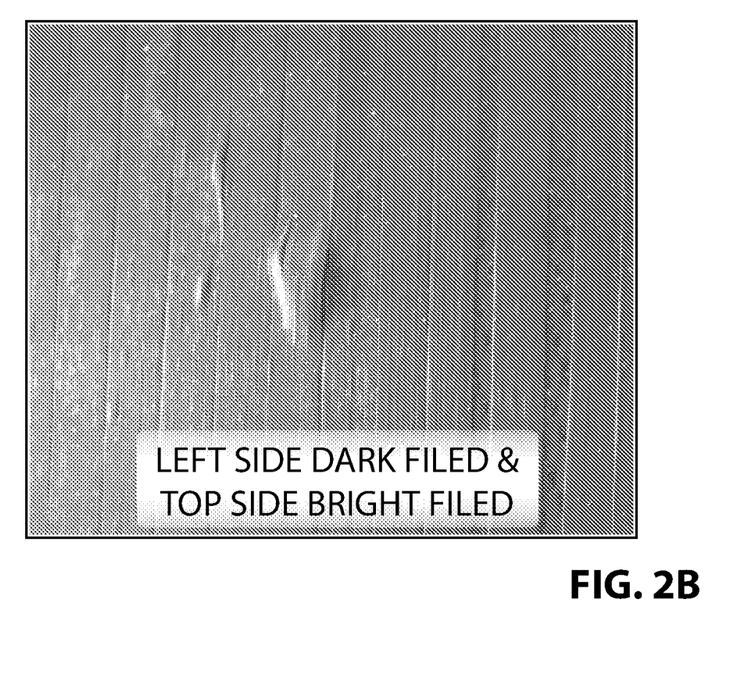
FIG. 2b is an exemplary image the surface of the composite component captured while the surface is illuminated with left side dark-field illumination and top side bright-field illumination.

FIGS. 2a and 2b illustrate the difference between having only dark-field illumination and having a combination of bright-field and dark-field illumination. FIG. 2a shows an image of a surface illuminated only with a left side illumination light source 104 and no top illumination light. FIG. 2b shows an image of the same surface illuminated with a left side illumination light source 104 and a top illumination light source 102. Using the right proportion of dark field and bright field illumination, the shadow edges seen in FIG. 2a are reduced or substantially eliminated while preserving the high contrast of the image. The illumination system 101 is thus conceived specifically for an online system whereby images are processed in real-time and automatically.

The illumination system 101 may comprise a diffuser in order to create non-coherent light and thus avoid noise introduced by sparkling reflections over the fiber details (speckles) and strong casted shadows. The diffuser may be provided for the top illumination light source 102 and/or the side illumination light source 104. In order to increase the depth of field; the image acquisition device 100 may be provided with an aperture that closes a large portion of the optical field of the lens. A fast shutter speed (with a short opening time) may be used to ensure a short exposure time, so that the image is not blurred, as images are taken while the surface is moving. A light source with a very fast response time may be used to allow precise synchronization with the shutter speed of the image acquisition device 100. In addition, the settings for the image acquisition device 100, such as the shutter speed and the aperture size; may be different from image to image and may change in real time.

The automatic adjustment of settings allows the quality of the images captured by the image acquisition device to be consistent while capturing images of different surface particularities, such that they may be inspected in an automated mode in real time while the surface is moving.

Figure 3:
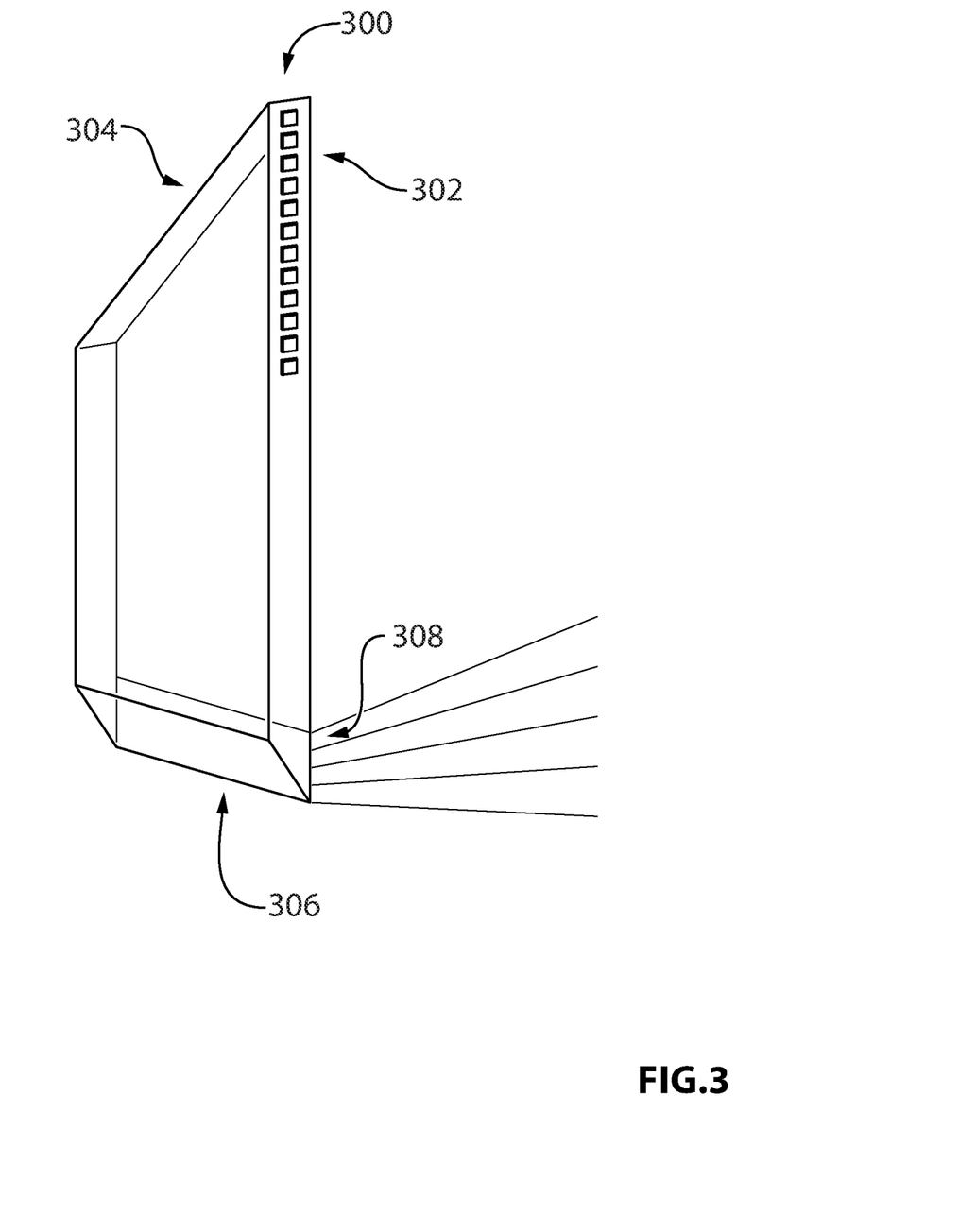
FIG. 3 is an exemplary embodiment of a light guide used as an illumination source.

In some embodiments, the top illumination source 102 and/or the side illumination source 104 comprises a light guide 300 as illustrated in FIG. 3. The light guide 300 may be composed of a prism and multiple mirrors. An LED (Light Emitting Diode) light source 302 is provided on at least one side edge of the light guide 300. A primary scattering mirror 304 is providing along a top edge of the light guide 300 while a secondary scattering mirror 306 is provided along a bottom edge thereof. The light guide can be a prism as illustrated or a long bundle made of fiber optics. An exit scattering window 308 allows scattered (i.e. very diffuse light) light to exit from the bottom edge of the light guide 300. Alternatively or in combination with the light guide 300, the top illumination source 102 and/or the side illumination source 104 comprises an LED array illumination plate. The plate may be straight or curved to widen the field of view. The LEDs in the array may also be modulated in intensity in order to provide an even illumination field. In other words, each LED in the array may have its intensity set independently to obtain the desired illumination field. Alternatively or in combination with the light guide 300, and/or the LED array illumination plate, the top illumination source 102 and/or the side illumination source 104 comprises a liquid crystal display (LCD) back illumination system, referred to herein as a backlighting plate. A backlighting plate may thus provide a very even illumination field with a high level of diffusibility, and include the side illumination source 104 and the light guide in one compact feature. The backlighting plate may also be curved and/or have individual nano-imprinted micro lenses regulated to a desired intensity level.

In some embodiments, the intensity of the light sources (side and/or top) may be too high to provide continuous illumination as this may cause the surface 106 to burn or be cured. Flash LED illumination may be used. Such light sources have a very short response time and also emit "cold" light. The flash LED illumination intensity is usually at least one order of magnitude higher than of a continuous mode LED illumination, for the short time provided by the shutter, thus allowing for a brighter or more intense illumination system 101. In addition, the small dimension of flash LEDs allows installation in a dense array, thereby achieving very even light emissivity from the light source.

Figure 2C:
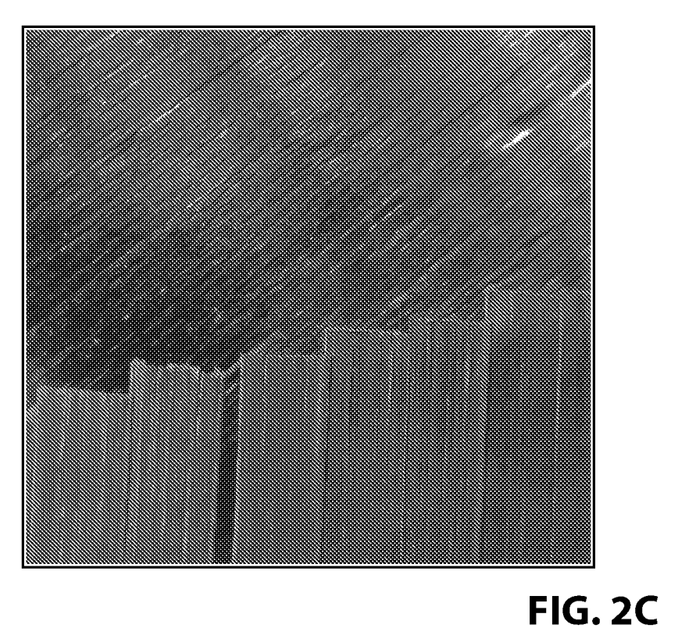
FIG. 2c is an exemplary image of the surface of the composite structure with a red-orange light illumination from the left side.
Figure 2D:
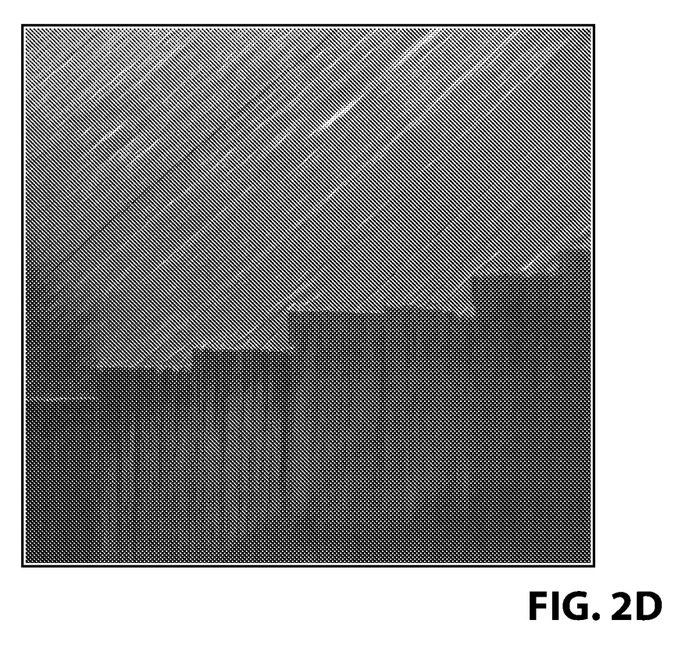
FIG. 2d is an exemplary image of the surface of the composite structure with a red-orange light illumination from the top side.

In some embodiments, the top illumination source 102 and/or the side illumination source 104 may be configured to project colored light onto the surface 106. Colors may be used to distinguish between layers of the composite structure. For example, when illuminating the surface 106 with a light frequency in the red-orange portion of the visible light spectrum, light absorption is very high and strongly dependent on fiber orientation. Different plies of the structure may thus be revealed using red-orange light using fiber orientation. The last ply of the ply lay-up may be visually "detached" from the previous ply using red-orange light. FIGS. 2c and 2d are exemplary embodiments of the composite structure imaged with a red-orange light. In FIG. 2c, the red-orange light is provided only from the side illumination source 104 while in FIG. 2d, the red-orange illumination is provided only from the top illumination source 102. As shown, in both cases, the last ply is clearly distinguished from the previous ply.

The red-orange light may be provided at a wavelength of about 625 nm to about 775 nm. In some embodiments, orange light at a wavelength of about 590 nm may be used. In some embodiments, red light at a wavelength of about 650 nm may be used. In some embodiments, red-orange light at a wavelength of about 621 nm may be used. In another example, blue light can be used to create high contrast images due to the high reflectivity of the AFP surface. Blue light may be provided at a wavelength of about 425 nm to about 490 nm. In some embodiments, blue light may be provided at a wavelength of about 475 nm. Other colors may also be used, as a function of a desired reflectivity and/or absorption of the light on the material. Color may be chosen based on the material of the composite structure, and/or the color of the material, and/or based on the desired purpose of the lighting and image acquisition, i.e. to distinguish between plies or to highlight certain details on the surface of the structure. Colored light may be used in combination with white light in order to create a desired effect.

In some embodiments, the top illumination source 102 and/or the side illumination source 104 may be configured to project infrared light onto the surface 106. When the surface is pre-heated by a heat lamp to improve tackiness, the last ply of carbon is hot from the compaction roller. A camera can be set to acquire images in the infrared domain in order to distinguish the hot layer from the background, similarly to the embodiment with red-orange illumination.

As shown in FIG. 1, the surface 106 of the composite structure may be curved, thus introducing parallax errors into the images. Parallax errors may be minimized by having a small field of vision, a vision direction that is perpendicular to the surface, a small angle of vision (or long vision distance), and/or inspection performed very close to the surface. When imaging the surface of a composite structure manufactured by AFP, the vision field cannot be reduced beyond a certain size imposed by the ply lay-up geometry. The free space close to the compaction roller is limited, thus complicating installation of the camera near the surface of the composite structure and with the vision direction perpendicular to the surface. In addition, a long vision distance also makes installing the camera in proximity to the compaction roller a challenge. As a result, in some embodiments, the online inspection system is provided with an optical adapter positioned between the image acquisition device and the surface of the composite structure for spacing the image acquisition device from the surface and directing a vision axis of the image acquisition device substantially perpendicularly to the surface. The image acquisition device may thus be mounted to the head of the tool and a long focal length is used for the image acquisition device.

Figure 4:
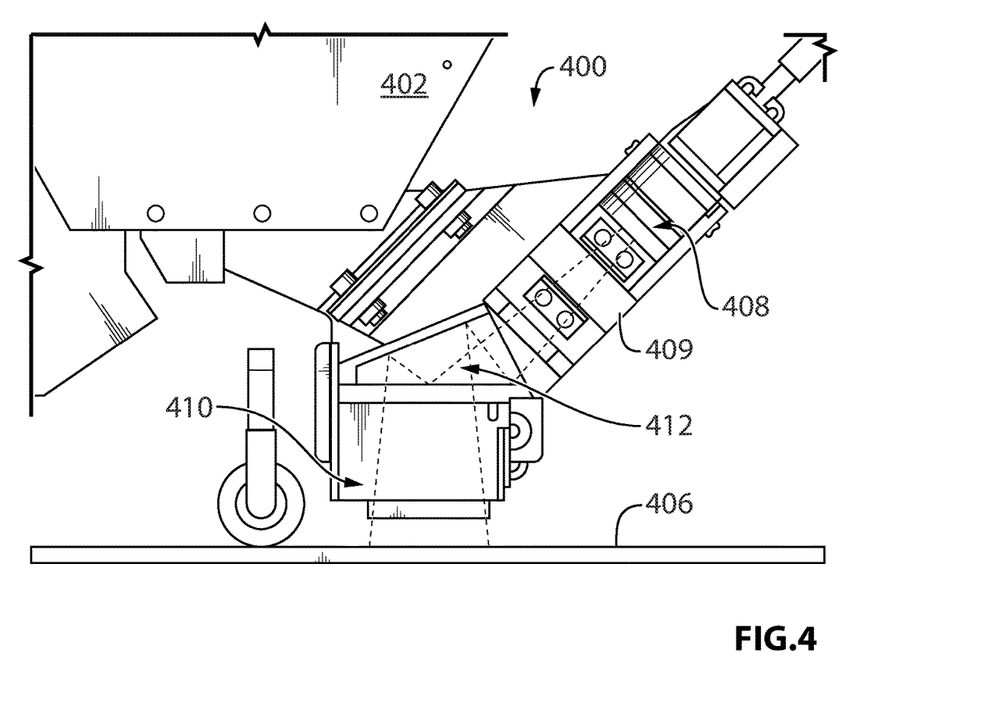
FIG. 4 is an exemplary embodiment of a system for online inspection having an optical adapter.

FIG. 4 is a side view of an exemplary embodiment of an online inspection system 400 having a long focal length and an optical adapter. A camera 408 provided with a lens having a long focal length is mounted to the AFP lay-up head 402. The optical adapter 412 spaces the camera 408 from the surface 406 and directs a vision axis of the camera 408 substantially perpendicularly to the surface 406. The spacing of the camera 408 from the surface 406 also allows room for the illumination system 410 below the camera 408 and above the surface 406. The illumination system 410 and the optical adapter 412 may be provided in a single housing 409. In some embodiments, the housing may be a darkroom enclosure, in order to block out all ambient light and allow for better control of light projected onto the surface 406 of the composite structure. Alternatively, the housing 309 may enclose only the illumination system 410, and the optical adapter 412 may be provided separately therefrom.

The optical adapter 412 may be composed of one or more optical elements for directing the vision axis of the image acquisition device perpendicularly to the surface being imaged. For example, the optical adapter 412 may be composed of a half-penta prism or a pair of mirrors. Other optical elements may also be used.

In some embodiments, the online inspection system 400 is provided with a long vision distance, a short shutter time, a closed aperture, high intensity illumination, very diffuse illumination, no light coherency or very low light coherency of the light beam, a shallow angle illumination very close to the surface, a top side illumination in conjunction with a shallow angle illumination, a flash illumination light source having a very fast response, and light emitted at a specific wavelength to detach the last ply from the background. While it may seem that diffuse light sources are readily available, the level of diffusibility required by the composite surface is much higher than what is currently available. This is due to the very small dimension of the fibers, which can easily create speckle if the illumination light is even only a little bit coherent.

Figure 5A:
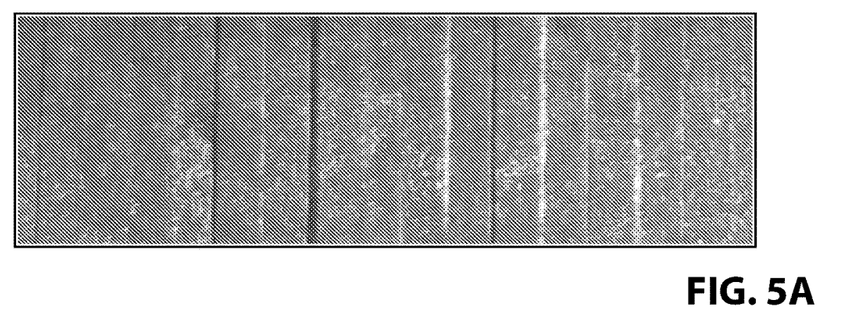
FIG. 5a is an exemplary image of the surface of a composite component without any pre-processing.
Figure 5B:
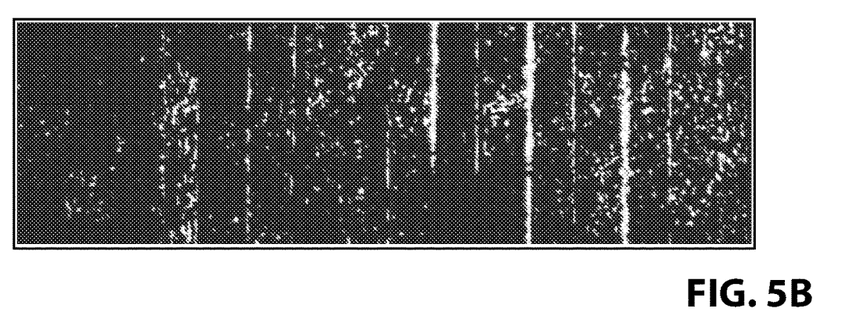
FIG. 5b is the image of FIG. 5a with standard pre-processing.
Figure 5C:
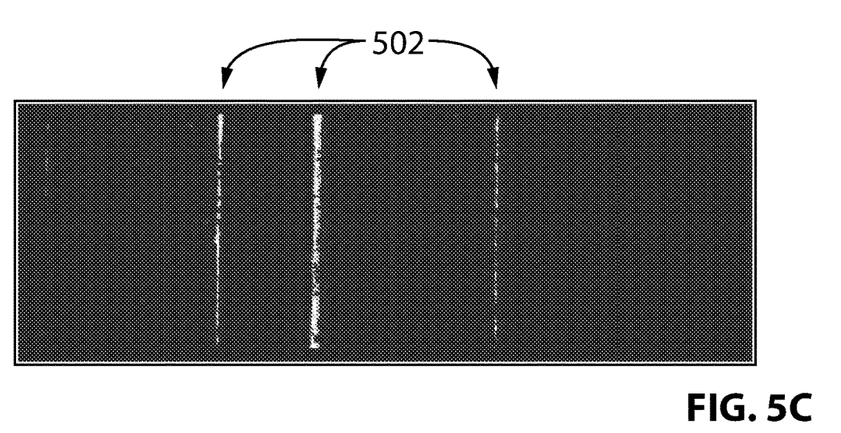
FIG. 5c is the image of FIG. 5a with color inversion pre-processing.

In some embodiments, color inversion is used to enhance a contrast between the dark features of the composite structure and the dark background. Color inversion facilitates filtering of the background of the image after feature extraction without losing useful information. Color inversion may be particularly useful when the features themselves are black and the background is black, thus having very low contrast. FIG. 5a is an example of an original image as captured by an image acquisition device of an online inspection system. In this example, the objective is to detect gaps in the surface of the composite structure. FIG. 5b is an example of the original image after standard preprocessing typically applied to the image. As shown, many features can be seen on the image, not only the gaps. FIG. 5c is an example of the original image with color inversion. The gaps 502 are clearly shown without additional features in the image. The level of filtering may be automated since the feature to background ratio can be optimized in a feedback loop of the processor.

Figure 6:
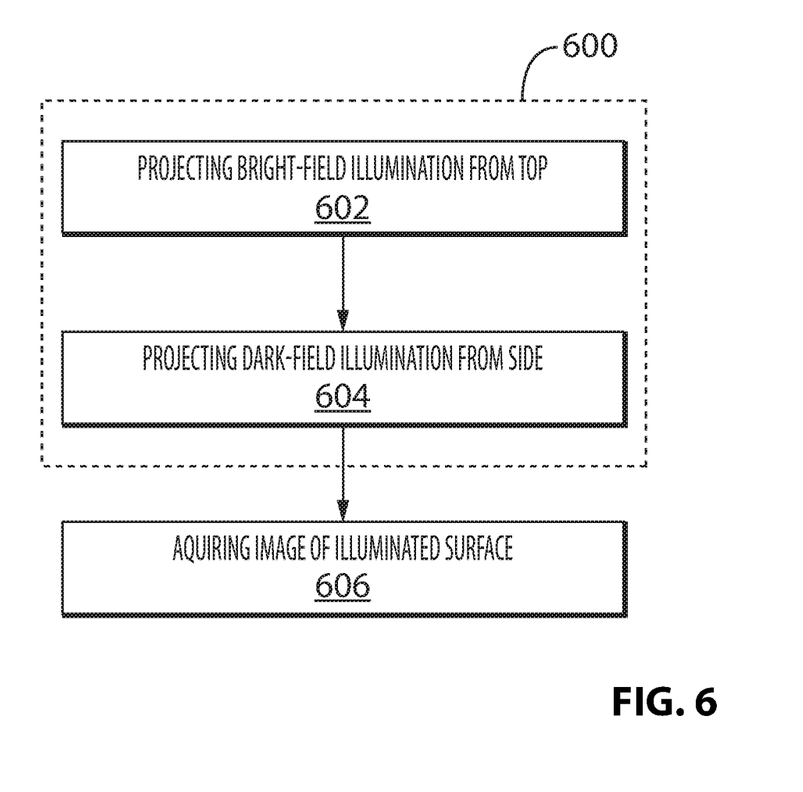
FIG. 6 is a flowchart of an exemplary method for the image acquisition phase of the online inspection of a composite structure manufactured by an automated tool.

FIG. 6 is a flowchart of an exemplary embodiment of a method for online inspection of a composite structure manufactured by an automated tool. The method comprises a first step 600 of illuminating the surface of the composite structure followed by a step 606 of acquiring at least one image of the illuminated surface. The illumination step 600 may be composed of a step 602 of projecting bright-field illumination onto the surface of the composite component and a step 604 of projecting dark-field illumination onto the surface of the composite component. The bright-field illumination is provided by a top illumination light source at a first intensity and the dark-field illumination is provided by a side illumination light source at a second intensity different from the first intensity. The two intensities are adjusted to provide a suitably contrasted image without too much shadow, in order to allow an image processor to detect features in the image and/or perform measurements in the image. The bright field illumination and the dark field illumination steps can be applied simultaneously or in sequence one after the other (but in the same shutter opening). The sequence application may be used if different colors are used for dark field and bright field illumination, to avoid unpredictable subtractive or additive color formation.

In some embodiments, acquiring at least one image comprises acquiring a sequence of multiple images. Each one of the images in the sequence may be acquired with a different and customized illumination strategy. The illumination strategy may be selected/applied in accordance with a specific local morphology of the surface of the composite structure. The method may thus be adapted in real time to the surface of the composite component, and inspection may be performed in an automated manner.

As stated above, the image acquisition device may be mounted to the head of the automated tool. Alternatively, the image acquisition device may be built into the head of the tool. The image processor may be provided remotely from the image acquisition device, thus allowing the portion of the system attached to the head of the automated tool to remain lightweight and small in volume. Color inversion image preprocessing may be used for the detection of certain types of features. Color inversion may be applied directly by the image processor or by an intermediate device receiving the acquired image from the image acquisition device, such as a Programmable Logic Controller (PLC), an upper level controller, etc.

The methods and systems described herein allow for real-time inspection of freshly laid fiber in a timely manner. The high volume of features and locations on the composite structure requires speed so as to account for changes in surface reflectivity as the surface of the composite structure dries. The means described herein used to enhance the contrast of the features under inspection, such as light frequencies, illumination type, and angles of illumination, allow high quality images to be acquired for a quick and automated inspection process.

The above description is meant to be exemplary only, and one skilled in the relevant arts will recognize that changes may be made to the embodiments described without departing from the scope of the invention disclosed. For example, the blocks and/or operations in the flowcharts and drawings described herein are for purposes of example only. There may be many variations to these blocks and/or operations without departing from the teachings of the present disclosure. For instance, the blocks may be performed in a differing order, or blocks may be added, deleted, or modified. The structure illustrated is thus provided for efficiency of teaching the present embodiment. The present disclosure may be embodied in other specific forms without departing from the subject matter of the claims. Also, one skilled in the relevant arts will appreciate that while the systems and methods disclosed and shown herein may comprise a specific number of elements/components, the systems and methods may be modified to include additional or fewer of such elements/components. The present disclosure is also intended to cover and embrace all suitable changes in technology. Modifications which fall within the scope of the present invention will be apparent to those skilled in the art, in light of a review of this disclosure, and such modifications are intended to fall within the appended claims.

The invention claimed is:

1. A system for online inspection of a composite structure manufactured by an automated tool, the system comprising:
  an image acquisition device in proximity to a head of the tool above a surface of the composite structure and defining a field of view on the surface of the composite structure, the image acquisition device and the surface of the composite structure defining a bright-field illumination zone and a dark-field illumination zone;
  an illumination system positioned above the surface of the composite structure and comprising:
    a top illumination light source inside the bright-field illumination zone, for projecting light at a first intensity onto the surface of the composite structure within the field of view that is reflected by the surface towards the image acquisition device; and
    a side illumination light source inside the dark-field illumination zone, for projecting light at a second intensity different from the first intensity onto the surface of the composite structure within the field of view that is reflected by the surface away from the image acquisition device;
  an optical adapter positioned between the image acquisition device and the surface of the composite structure for directing a vision axis of the image acquisition device substantially perpendicularly to the surface; and
  an enclosure housing at least the illumination system and coupled to the image acquisition device, the enclosure blocking out ambient light and providing control of light onto the surface of the composite structure;
  wherein the field of view on the surface is simultaneously illuminated by a combination of the top illumination light source and the side illumination light source by a combination of bright field and dark field illumination, and the light from the top illumination light source fills edges of shadows created by the side illumination light source;
  wherein only one of the top illumination light source and the side illumination light source projects red-orange colored light onto the surface to distinguish between plies of the composite structure based on fiber orientation;
  wherein said only one of the top illumination light source and the side illumination light source comprises an array of flash Light Emitting Diodes (LEDs) having an illumination intensity at least one order of magnitude greater than a continuous mode of LED illumination.

2. The system of claim 1, wherein the enclosure houses the optical adapter and the illumination system.

3. The system of claim 1, wherein the image acquisition device comprises a lens having a long focal length F and a corresponding viewing distance D.

4. The system of claim 3, wherein the long focal length F is at least five times longer than a diagonal of one of a film plane and a digital sensor of the image acquisition device.

5. The system of claim 4, wherein the viewing distance D is at least twenty times longer than the diagonal of one of the film plane and the digital sensor of the image acquisition device.

6. The system of claim 1, wherein the array of LEDs is at least one of curved and composed of LEDs of varying intensities.

7. The system of claim 1, wherein at least one of the top illumination light source and the side illumination light source comprises a backlighting plate.

8. The system of claim 1, wherein the image acquisition device comprises a shutter time synchronized with a response time of the illumination system.

9. The system of claim 1, wherein the optical adapter is positioned between the image acquisition device and the surface of the composite structure for spacing the image acquisition device from the surface.

10. The system of claim 1, wherein the red-orange colored light is at a wavelength of about 621 nm or about 625 nm to about 775 nm.

11. A method for online inspection of a composite structure manufactured by an automated tool, the method comprising:

providing an illumination system comprising a top illumination light source and a side illumination light source;
illuminating a surface of the composite structure by:
projecting light at a first intensity onto the surface of the composite structure from the top illumination light source; and
projecting light at a second intensity different from the first intensity onto the surface of the composite structure from the side illumination light source;
acquiring at least one image of the illuminated surface of the composite structure using an image acquisition device in proximity to a head of the automated tool, the image acquisition device and the surface of the composite structure defining a bright-field illumination zone comprising the top illumination light source and a dark-field illumination zone comprising the side illumination light source; and
directing a vision axis of the image acquisition device substantially perpendicularly to the surface with an optical adapter;
wherein the illumination system is comprised in an enclosure coupled to the image acquisition device, the method further comprising:
blocking out ambient light and providing control of light onto the surface of the composite structure with the enclosure;
wherein the field of view on the surface is simultaneously illuminated by a combination of the top illumination light source and the side illumination light source by a combination of bright field and dark field illumination, and the light from the top illumination light source fills edges of shadows created by the side illumination light source
wherein only one of the top illumination light source and the side illumination light source projects red-orange colored light onto the surface to distinguish between plies of the composite structure based on fiber orientation,
wherein said only one of the top illumination light source and the side illumination light source comprises an array of flash Light Emitting Diodes (LEDs) having an illumination intensity at least one order of magnitude greater than a continuous mode of LED illumination.

12. The method of claim 11, wherein the optical adapter and the illumination system are comprised in the enclosure coupled to the image acquisition device.

13. The method of claim 11, wherein acquiring an image comprises acquiring the image with a long focal length F in a telephoto domain and a corresponding viewing distance D.

14. The method of claim 13, wherein the long focal length F is at least five times longer than a diagonal of one of a film plane and a digital sensor of the image acquisition device.

15. The method of claim 14, wherein the viewing distance D is at least twenty times longer than the diagonal of one of the film plane and the digital sensor of the image acquisition device.

16. The method of claim 11, wherein the array of LEDs is at least one of curved and composed of LEDs of varying intensities.

17. The method of claim 11, wherein at least one of the top illumination light source and the side illumination light source comprises a backlighting plate.

18. The method of claim 11, wherein acquiring at least one image comprises acquiring a sequence of multiple images, each one with a different and customized illumination strategy applied in accordance with a specific local morphology of the surface of the composite structure.

19. The method of claim 11, wherein illuminating the surface of the composite structure comprises projecting light at the first intensity and projecting light at the second intensity in a sequential manner.

20. The method of claim 11, wherein the red-orange colored light is at a wavelength of about 621 nm or about 625 nm to about 775 nm.

* * * * *